(12) United States Patent
Palmer

(10) Patent No.: US 6,559,118 B1
(45) Date of Patent: May 6, 2003

(54) FRAGRANCE COMPOUNDS

(75) Inventor: Kenneth Palmer, Kent (GB)

(73) Assignee: Quest International B.V., Naarden (NL)

( * ) Notice: Subject to any disclaimer, the term of this patent is extended or adjusted under 35 U.S.C. 154(b) by 0 days.

(21) Appl. No.: 09/980,855

(22) PCT Filed: Jun. 26, 2000

(86) PCT No.: PCT/GB00/02443

§ 371 (c)(1),
(2), (4) Date: Dec. 7, 2001

(87) PCT Pub. No.: WO01/00551

PCT Pub. Date: Jan. 4, 2001

(30) Foreign Application Priority Data

Jun. 28, 1999 (EP) .............................. 99305074

(51) Int. Cl.$^7$ ............................ A61K 7/46; C07C 35/18
(52) U.S. Cl. ............................ 512/25; 512/8; 568/700; 568/822; 568/823; 568/825
(58) Field of Search ....................... 512/8, 25; 568/700, 568/822, 823, 825

(56) References Cited

U.S. PATENT DOCUMENTS 4,250,342 A  2/1981  Sprecker et al.

FOREIGN PATENT DOCUMENTS

| EP | 0 199 330 | 10/1986 |
| GB | 1372 021 | 10/1974 |
| NL | 8 701 489 | 1/1989 |

*Primary Examiner*—Jill Warden
*Assistant Examiner*—Monique T. Cole
(74) *Attorney, Agent, or Firm*—Morgan, Lewis & Bockius LLP

(57) ABSTRACT

Novel compounds having the structure (I) where $R_1$ is a lower alkyl group, $R_2$, $R_3$, $R_4$ and $R_5$ is each independently hydrogen or a lower alkyl group, $R_6$ is hydrogen, a lower alkyl group, an alkylidene group or a lower alkenyl group and $R_7$ is hydrogen or a lower alkyl group, have desirable odor properties, possibly of a blackcurrant, green, buchu, cassis nature, and find use in perfumes and perfumed products.

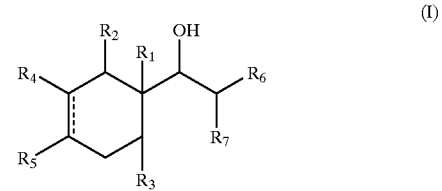

(I)

9 Claims, No Drawings

FRAGRANCE COMPOUNDS

FIELD OF THE INVENTION

This invention concerns novel fragrance compounds, and perfumes and perfumed products comprising the novel compounds.

SUMMARY OF THE INVENTION

In one aspect, the present invention provides a compound having the structure

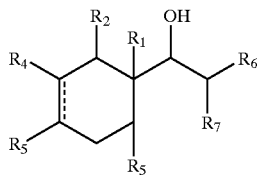

where $R_1$ is a lower alkyl group, $R_2$, $R_3$, $R_4$ and $R_5$ is each independently hydrogen or a lower alkyl group, $R_6$ is hydrogen, a lower alkyl group, an alkylidene group or a lower alkenyl group and $R_7$ is hydrogen or a lower alkyl group.

For brevity and simplicity, such materials will be referred to as "the compound", "the novel compound" or "the compound of the invention".

The compounds of the invention may exist in a number of isomeric forms, and the invention includes within its scope each individual isomer and also mixtures of isomers.

The term "lower alkyl" is used in this specification to mean an alkyl group having from 1 to 4 carbon atoms.

The term "lower alkenyl" is used in this specification to mean an alkenyl group having from 1 to 4 carbon atoms.

The compounds of the invention can possess fragrance or odour properties which are generally regarded as interesting, pleasant or attractive.

The currently preferred compound in accordance with the invention has $R_1$, $R_2$, $R_5$, $R_6$ and $R_7=CH_3$; $R_3$ and $R_4=H$, with a double bond in the ring at the 34 position. This compound thus has the structure

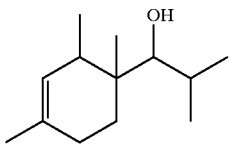

and is 2-methyl-1-(1,2,4-trimethyl-3-cyclohexen-1-yl)-1-propanol. For brevity this compound is referred to herein as compound 1. Compound 1 has desirable odour properties, generally of a blackcurrant, green, buchu, cassis nature, and appears to have good substantivity. The compound also has good performance against kitchen malodour. Materials having cassis odour are of great interest to the fragrance industry, with such materials, eg Neocaspirene (described in U.S. Pat. No. 4537702), generally being of high value. Naturally occurring materials with cassis odour contain sulphur and the commonest synthetic materials with cassis odour contain sulphur or oximes. Compounds of the invention thus have the advantage of lacking sulphur or oximes. Compounds of the invention also constitute the first known alcohols having cassis odour.

Further compounds of the invention include the following:

| Structure | Odour (Dry) | Odour (Fresh) |
|---|---|---|
| 1-(1,2-dimethyl-3-cyclohexen-1-yl)-2-methyl-1-propanol | Strong Celery | Strong Earthy<br>Medium Potato<br>Medium Green |
| 1-(1,3-dimethyl-3-cyclohexen-1-yl)-2-methyl-1-propanol | Medium Fruity<br>Medium Floral<br>Weak Earthy | Strong Metallic<br>Medium Floral<br>Medium Herbal |
| 2-methyl-1-(1,3,4-trimethyl-3-cyclohexen-1-yl)-1-propanol | Medium Minty<br>Medium Fruity<br>Weak Floral | Medium Fruity<br>Medium Fatty |
| 2-methyl-1-(1,2,4-trimethylcyclohexyl)-1-propanol | Weak Woody<br>Weak Patchouli<br>Weak Grapefruit/<br>Rhubarb | Weak Earthy<br>Weak Minty<br>Weak Camphoraceous |
| 2-methyl-1-(1,2,4-trimethyl-3-cyclohexen-1-yl)-3-buten-1-ol | Fruity<br>Cassis | Fruity<br>Cassis |
| 2-methyl-1-(1,2,4-trimethyl-3-cyclohexen-1-yl)-1-butanol | Fruity<br>Green<br>Cassis | Fruity<br>Green<br>Cassis |
| 2-methyl-1-(1,2,4,6-tetramethyl-3-cyctohexen-1-yl)-2-propen-1-ol | Woody<br>Patchouli | Earthy<br>Woody<br>Patchouli |
| 2-methyl-1-(1,2,4,6-tetramethyl-3-cyclohexen-1-yl)-1-propanol | Woody<br>Herbal<br>Cassis | Woody<br>Herbal<br>Cassis |
| 2-methyl-1-(1,2,4-trimethyl-3-cyclohexen-1-yl)-2-propen-1-ol | Strong Herbal<br>Strong Sweet<br>Strong Minty<br>Cassis | Strong Herbal<br>Strong Earthy<br>Strong Minty |

| | Odour (Dry) | Odour (Fresh) |
|---|---|---|
| 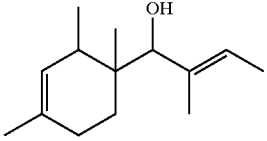<br>2-methyl-1-(1,2,4,trimethyl-3-cyclohexen-1-yl)-2-buten-1-ol | Medium Fruity<br>Medium Buchu<br>Medium Cassis | Medium Green<br>Medium Herbal |
| 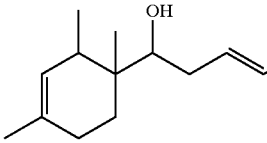<br>1-(1,2,4-trimethyl-3-cyclohexen-1-yl)-3-penten-1-ol | Medium Fruity<br>Medium Cassis | Medium Fruity<br>Medium Minty |
| 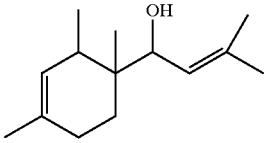<br>3-methyl-1-(1,2,4-trimethyl-3-cyclohexen-1-yl)-2-buten-1-ol | Medium floral<br>Medium Salicylate | Medium Fruity<br>Medium Green<br>Medium Floral |
| 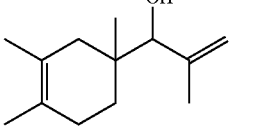<br>2-methyl-1-(1,3,4-trimethyl-3-cyclohexen-1-yl)-2-propen-1-ol | Fruity<br>Green | Green<br>Fruity |
| 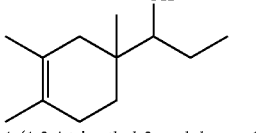<br>1-(1,3,4-trimethyl-3-cyclohexen-1-yl)-1-propanol | Aniseed<br>Herbal<br>Orris | Fruity<br>Aniseed<br>Orris |

The odour properties of the compounds of the invention mean that a compound or mixture of compounds in accordance with the invention may be used as such to impart, strengthen or improve the odour of a wide variety of products, or may be used as a component of a perfume (or fragrance composition) to contribute its odour character to the overall odour of such perfume. The compounds are stable and substantive. For the purposes of this invention a perfume is intended to mean a mixture of fragrance materials, if desired mixed with or dissolved in a suitable solvent or mixed with a solid substrate, which is used to impart a desired odour to the skin, hair and/or product for which an agreeable odour is indispensable or desirable. Example of such products are: fabric washing powders, washing liquids, fabric softeners and other fabric care products; detergents and household cleaning, scouring and disinfection products; air fresheners, room sprays and pomanders; soaps, bath and shower gels, shampoos, hair conditioners and other personal cleansing products; cosmetics such as creams, ointments, toilet waters, preshave, aftershave, body, skin and other lotions, talcum powders, body deodorants and antiperspirants, etc.

Other fragrance materials which can be advantageously combined with one or more compounds according to the invention in a perfume are, for example, natural products such as extracts, essential oils, absolutes, resinoids, resins, concretes etc., but also synthetic materials such as hydrocarbons, alcohols, aldehydes, ketones, ethers, acids, esters, acetals, ketals, nitrites, etc., including saturated and unsaturated compounds, aliphatic, carbocyclic, and heterocyclic compounds.

Such fragrance materials are mentioned, for example, in S. Arctander, Perfume and Flavor Chemicals (Montclair, NJ., 1969), in S. Arctander, perfume and Flavor Materials of Natural Origin (Elizabeth, N.J., 1960) and in "Flavor and Fragrance Materials—1991", Allured Publishing Co. Wheaton, Ill. USA.

Examples of fragrance materials which can be used in combination with one or more compounds according to the invention are: geraniol, geranyl acetate, linalol, linalyl acetate, tetrahydrolinalol, citronellol, citronellyl acetate, dihydromyrcenol, dihydromyrcenyl acetate, tetrahydromyrcenol, terpineol, terpinyl acetate, nopol, nopyl acetate, 2-phenyl-ethanol, 2-phenylethyl acetate, benzyl alcohol, benzyl acetate, benzyl salicylate, styrallyl acetate, benzyl benzoate, amyl salicylate, dimethylbenzylcarbinol, trichloromethylphenylcarbinyl acetate, p-tert-butylcyclohexyl acetate, isononyl acetate, vetiveryl acetate, vetiverol, α-hexylcinnamaldehyde, 2-methyl-3p-tert-butylphenyl)propanal, 2-methyl-3-(p-isopropylphenyl) propanal, 2-(p-tert-butylphenyl)-propanal, 2,4-dimethyl-cyclohex-3-enyl-carboxaldehyde, tricyclodecenyl acetate, tricyclodecenyl propionate, 4(4-hydroxy-4-methylpentyl)-3-cyclohexenecarboxyaldehyde, 4-(4-methyl-3-pentenyl)-3-cyclohexenecarboxaldehyde, 4-acetoxy-3-pentyl-tetrahydropyran, 3-carboxymethyl-2-pentylcyclopentane, 2-n-heptylcyclopentanone, 3-methyl-2-pentyl-2-cyclopentenone, n-decanal, n-dodecanal, 9decen-1-ol, phenoxyethyl isobutyrate, phenylacetaldehyde dimethyl acetal, phenylacetaldehyde diethyl acetal, geranyl nitrile, citronellyl nitrile, cedryl acetate, 3-isocamphylcyclohexanol, cedryl methyl ether, isolongifolanone, aubepine nitrile, aubepine, heliotropin, coumarin, eugenol, vanillin, diphenyl oxide, hydroxycitronellal, ionones, methylionones, isomethylionones, irones, cis-3-hexenol and esters thereof, indan musks, tetralin musks, isochroman musks, macrocyclic ketones, macrolactone musks, ethylene brassylate.

Solvents which can be used for perfumes which contain a compound according to the invention are, for example: ethanol, isopropanol, diethyleneglycol monoethyl ether, dipropylene glycol, diethyl phthalate, triethyl citrate, isopropyl myristate, etc.

The quantities in which one or more compounds according to the invention can be used in perfumes or in products to be perfumed may vary within wide limits and depend, inter alia, on the nature of the product, on the nature and the quantity of the other components of the perfume in which the compound is used and on the olfactive effect desired. It is therefore only possible to specify wide limits, which, however, provide sufficient information for the specialist in the art to be able to use a compound according to the invention, for his specific purpose. Typically, a perfume comprises one or more compounds in accordance with the invention in an olfactively effective amount. In perfumes an amount of at least 0.01% by weight or more of a compound according to the invention will generally have a clearly perceptible olfactive effect. Preferably the amount is in the range 0.1 to 80% by weight, more preferably at least 1%. The amount of the compound according to the invention present in products will generally be at least 10 ppm by weight, preferably at least 100 ppm, more preferably at least 1000 ppm. However, levels of up to about 20% by weight may be used in particular cases, depending on the product to be perfumed.

In a further aspect the invention provides a perfume comprising one or more compounds of the invention in an olfactively effective amount.

The invention also covers a perfumed product comprising one or more compounds of the invention.

The compounds of the invention may be synthesised by reaction of an appropriate aldehyde with a Grignard reagent to give a substituted alcohol. For example, compound 1 can be prepared by reaction of 1,2,4-trimethyl-3-cyclohexene-1-carboxaldehyde with isopropylmagnesium bromide or isopropylmagnesium chloride, as follows (Reaction 1)

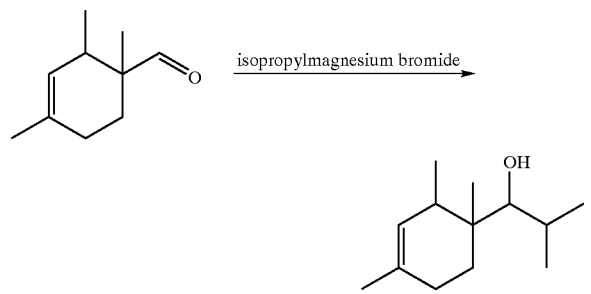

In a further aspect of the invention there is thus provided a method of making a compound in accordance with the invention, comprising a Grignard reaction of the aldehyde.

The aldehyde may be prepared via Diels-Alder chemistry. For example, 1,2,4-trimethyl-3-cyclohexene-1-carboxaldehyde can be prepared by reaction between 2-methyl-1,3-pentadiene and methacrolein (the latter conveniently being produced by Mannich chemistry).

The compounds of the invention may alternatively be synthesised by reduction of the corresponding ketone. For example, compound 1 can be prepared by reduction of 2-methyl-1-(1,2,4-trimethyl-3-cyclohexen-1-yl)-1-propanone (referred to for simplicity as molecule A), eg using lithium aluminium hydride in ether, as follows (Reaction 2)

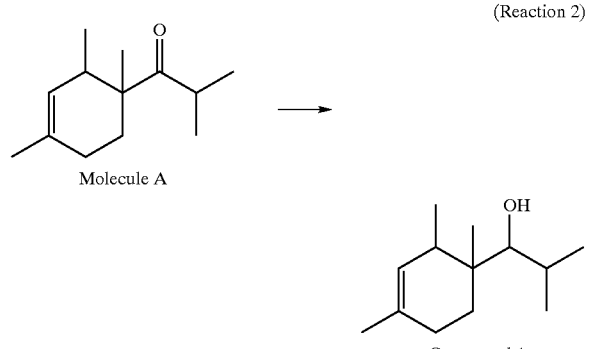

A further aspect of the invention is thus a method of making a compound in accordance with the invention, comprising reduction of a ketone.

The corresponding ketone may be prepared by reaction of an appropriate diene and dieneophile in a Diels-Alder reaction. For example, molecule A may be produced by Diels-Alder reaction of 2-methyl-1,3-pentadiene and 2,4-dimethyl-1-penten-3-one (also referred to herein for convenience as molecule B), as follows (Reaction 3)

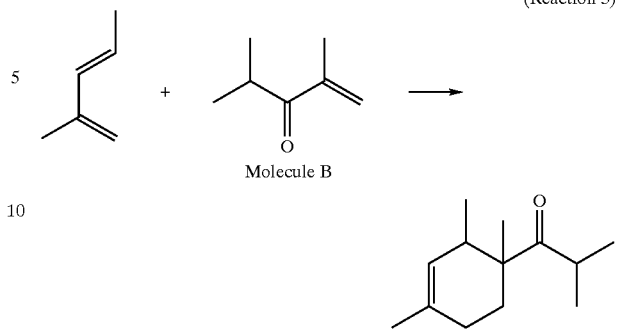

The Diels-Alder reaction may be performed in known manner and is preferably carried out as a thermal reaction, with the reactants heated together to obtain addition as the temperature rises, or under pressure, with the reactants being heated together in an autoclave or a pressurised plug flow reactor.

Molecule B may be synthesised in a number of ways, including

1. Reaction of methacrolein with isopropyl magnesium bromide in diethyl ether to give 2,4-dimethyl-1-penten-3-ol, followed by oxidation of the alcohol to the ketone using chromic acid, as follows (Reaction 4)

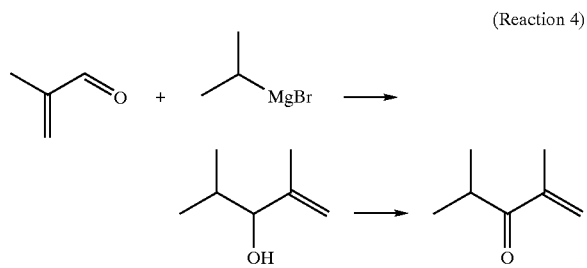

2. Bromination of 2,4-dimethyl-3-pentanone in chloroform (with simultaneous loss of HBr) to produce the bromoketone, 2-bromo-2,4-dimethyl-3-pentanone. Treatment of the bromoketone with 1,8-diazabicyclo [5.4.0] undec-7-ene (referred to as DBU for brevity) in dimethylformamide yields the desired molecule B, as follows (Reaction 5)

The invention will be further described, by way of illustration, in the following Examples.

GC/GCMS Conditions for analyses in the following Examples:
GC: Hewlett Packard HP 6890 gas chromatograph
Column: HP-5 (crosslinked 5% Phenylmethylsiloxane) 25m×0.2 mm (internal diameter)×0.33 μm (film thickness)

Carrier gas: Hydrogen
Temperature Prog: 50° C. (initial oven temperature) to 280° C. at a rate of 12° C./min
GCMS : Finnigan Ion Trap instrument
GC Column: J&W DB-5MS 30m×0.25 mm (internal diameter)×0.25 μm (film thickness)
GC Carrier Gas: Helium
GC Temperature Prog: 70° C. (initial oven temperature), ramp 40° C./min to 270° C., hold 10 minutes
MS uses an ion trap; 35–450 amu acquisition, 1 scan/second; source pressure 30 mTorr; electron impact 70 eV; positive ion mode.

EXAMPLE 1

2-methyl-1-(1,2,4-trimethyl-3-cyclohexen-1-yl)-1-propanol (compound 1) was prepared from 1,2,4-trimethyl-3-cyclohexene-1-carboxaldehyde and isopropylmagnesium bromide (reaction 1 above).

1,2,4-trimethyl-3-cyclohexene-1-carboxaldehyde was prepared by a Diels-Alder reaction between 2-methyl1,3-pentadiene and methacrolein (prepared by Mannich-chemistry). To this aldehyde (15 g, 0.1M) in 100 ml diethyl ether, cooled in an ice bath, was added via a syringe isopropylmagnesium bromide (60 ml, 2.0M solution in diethyl ether). The reaction mixture was stirred for 2 hours and allowed to warm to ambient temperature then poured slowly into a dilute aqueous solution of ammonium chloride. The organic phase was separated and the aqueous phase extracted with more diethyl ether (50 ml). The organic extracts were combined, washed with water, dried with magnesium sulphate, filtered and solvent removed via rotary evaporation (rotavap). The crude was analysed by GC then GCMS. 4 product peaks of relative peak area (hereinafter to as "rpa") 77.6%, 8.5%, 5.2% and 4.1% were shown to have MWs 154, 154, 196, 196, respectively. Hence the 2 major products were not the required isopropyl additions, but were comparable to the starting aldehyde being reduced to the corresponding alcohol, having the following structure:

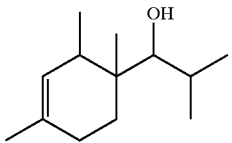

For convenience, this alcohol is referred to as molecule D.
$^{13}$C NMR (CDCl$_3$) (Molecule D) 16.1663(CH$_3$), 22.4234 (CH$_3$), 23.3565(CH$_3$), 27.3298(CH$_2$), 28.6985(CH$_2$), 356184(CH-tert), 37.760(C-quart), 68.0539(CH$_2$—OH), 126.4025(CH=), 132.2290(C[CH$_3$]=).

The combined product at this stage had a distinct cassis, buchu like odour. GC smelling indicated that this odour was coming from the 2 peaks at 5.2 and 4.1%, ie the required product. The 2 different materials (Molecule D and compound 1) were then separated using column chromatography (silica gel) eluting with hexane+10% diethyl ether. Both sets of products were then distilled using the bulb-to-bulb Kugelrohr technique. The distillation yielded approximately 0.5 g of Compound 1 (b.pt 80° C./0.1 mmHg (13.33 Nm$^{-2}$)). A second GCMS analysis of compound 1 indicated that it was composed of 3 peaks of 48.3%, 39.0% and 5.5%. The respective MWs were determined as 196, 196 and 198. Assessment of the 2 major peaks by GC smelling indicated that the isomer at 39.0% appeared to possess a stronger cassis, buchu-like odour than the 48.3% peak and hence would probably be the preferred isomer. However, when compound 1 was analysed on a HP Chiral-B (10% permethylatedbetacyclodextrin) 25 m×0.25 mm id column, 6 peaks were seen at rpa 48.8%, 20.1%, 5.6%, 13.8%, 2.6%, 2.6%. The chiral isomers of compound 1 can thus be partially separated.

EXAMPLE 2

2,4-dimethyl-1-penten-3-one (molecule B) was prepared via reaction 5 above.
Bromination of diisopropyl ketone
2,4-dimethyl-3-pentanone (330 g, 2.89M) in chloroform (800 ml) was cooled in an ice water bath to 10° C. and bromine (462 g, 2.89M) was added slowly over 3 hours. After the addition, a slow stream of nitrogen was introduced to the mixture and HBr gas was slowly evolved from the flask. The nitrogen was left bubbling over a weekend to remove all of the HBr produced and then sodium carbonate (5 g) was added. The reaction mixture was then filtered through Celite and the chloroform removed using a rotary evaporator. Distillation of the crude product using a 1' (2.54 cm) vigreux gave essentially pure 2-bromo-2,4-dimethyl-3-pentanone (478 g, 2.47M) b.pt. 50–52° C./10 mb (1000 Nm$_{-2}$).
Dehydrobromination with DBU
To a stirred solution of 2-bromo-2,4-dimethyl-3-pentanone (258 g, 1.33 M) in dimethylformamide (750 ml) was added over 30 mins 1,8-diazabicyclo[5.4.0]undec-7-ene (DBU) (200 g, 1.32M). The reaction was then stirred for 2 hours during which time the temperature rose to 45° C. and the reaction was then left to stand overnight at ambient temperature. The mixture was poured into 3L of hydrochloric acid solution (3%) and the organic phase which separated was extracted with pentane (300 ml). The aqueous phase was also extracted with pentane (300 ml), and the 2 pentane extracts combined, dried with magnesium sulphate and filtered. Pentane was then removed by distillation through a 1' (2.54 cm) vigreux at atmospheric pressure. b.pt up to 90° C., with continued distillation giving 2,4-dimethyl-1-penten-3one (molecule B ) (194 g, 1.73 M) b.pt 120–130° C. At this stage the pot temperature began to rise, but no more material was distilled although approx 50 g was left as a residue. GC analysis showed a single peak. After cooling the residue, a further distillation was carried out under reduced pressure with a new product distilling from the residue at b.pt. 72° C./0.2 mb (20 Nm $^{-2}$). GCMS indicated this material had MW 224 and was the product of hetero Diels-Alder reaction of the pentenone, as follows

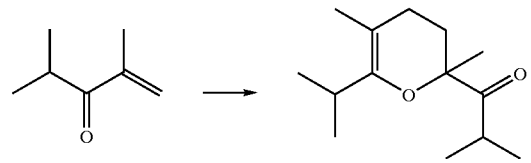

The product of the hetero Diels-Alder reaction, 1-(6-isopropyl-2,5-dimethyl-3,4-dihydro-2H-pyran-2-yl)-2-methyl-1-propanone, is referred to herein as molecule C for brevity.
$^{13}$C NMR (CDCl$_3$) of Molecule C 17.11(CH$_3$), 18.48 (CH$_3$), 19.43(CH$_3$), 19.62(CH$_3$), 20.22(CH$_3$), 22.12(CH$_3$), 24.33(CH$_2$), 28.20(CH-tert), 29.37(CH$_2$), 34.23(CH-tert), 81.09(C-quart), 98.87(C=C), 149.57(C=), 219.09(C=O).
Molecule B was then used in a Diels-Alder reaction with 2-methyl-1-3-pentadiene to produce 2-methyl-1-(1,2,4-trimethyl-3-cyclohexen-1-yl)-1-propanone (molecule A) (reaction 3 above).
Diels-Alder reactions of pentenone with methylpentadiene
1. Thermal method
A mixture of 2-methyl-1,3-pentadiene (41 g, 0.5M) and 2,4-dimethyl-1-penten-3-one (molecule B) (56 g, 0.5M) was heated to reflux which commenced at a pot temperature of 90° C. After 32 hours at reflux, the pot temperature had risen to 145° C. GC analysis showed that 9% of unreacted pentenone remained in the reaction mixture. An additional 10 g of 2-methyl-1,3-pentadiene was added and the reflux continued for a further 4 hours. GC analysis indicated 3 major peaks of rpa 11.8%, 15.4% and 61.4%, identified by GCMS as MWs 224, 194 and 194, respectively. The peak of MW 224 was identified as being molecule C, due to a hetero Diels-Alder reaction. The other peaks were of the correct molecular weight for the product of interest.

The reaction product was distilled using a 1' (2.54 cm) vigreux column and 67.2 g of the intermediate Diels-Alder adduct was obtained (b.pt 70–75° C./0.1 mbar (10 $Nm^{-2}$)). A pot residue of 30 g was also noted.

2. Autoclave method

A similar mixture to that used above but using 60 g of diene was charged to a Buchi autoclave and then heated to 180° C. for 3 hours before allowing to cool overnight. Distillation as above gave 72 g product which was shown by GC to comprise the same 3 peaks but of rpa 7.4%, 20.0%, 61.6%.

For both the thermal method and the autoclave method, the product comprises the desired molecule A, with molecule C as impurity.

$^{13}C$ NMR of molecule A 18.597($CH_3$), 19.798($CH_3$), 20.868($CH_3$), 21.498($CH_3$), 23.116($CH_3$), 24.363($CH_2$), 27.375($CH_2$), 34.861 (CH of isopropyl), 37.461 (CH tert), 49.511 (C quart), 125.21 (C=C), 131.219 (C=C), 220.184 (C=O).

The products of the thermal and autoclave Diels-Alder reactions were combined, and the combined product was reduced using lithium aluminium hydride in ether with acid work up so that the molecule A produced the desired product, compound 1, via reaction 2 above. Any molecule C impurity present formed a different product that was readily separable from compound 1 eg by fractional distillation.

Reduction and Purification

The combined product (comprising molecule A and molecule C) prepared as above (200 g, 1.03M) in diethylether (500 ml) was stirred with cooling in an ice bath and lithium aluminium hydride (20 g) was added carefully in pellet form over 15 mins. The reaction was slightly exothermic as it progressed and stirring was continued for 4 hours until all of the pellets appeared to have reacted. Maintaining the reaction vessel in an ice bath, hydrochloric acid (10% aqueous solution, 500 ml) was slowly added dropwise. The reaction product was then poured into a separating funnel and the organic diethyl ether phase removed. The aqueous phase was extracted with diethyl ether (100 ml) and the 2 extracts combined, washed with water, dried with magnesium sulphate, filtered and the solvent removed in vacuo to give crude product (209 g).

Combined GC/GCMS analysis of the crude gave the following results:

8 peaks were seen on GCMS: 4 with MW 226 (product of molecule C), 4 with MW 196 (compound 1). Standard GC only found 3 peaks for MW 196 (1). 1.6% Kovats 1308 MW 226 (2). 3.8% Kovats 1314 MW 226 (3). 2.0% Kovats 1358 MW 226 (4). 2.9% Kovat MW 226 (5). 55.6% Kovats 1417 MW 196 (6). 24.6% Kovats 1422 MW 196 (7). 3.7% Kovats 1430.

The peaks with MW 196 were various isomers of compound 1.

The crude product and material from an additional smaller scale reaction (total 334.5 g) was then distilled via a 0.5 m sulzer packed column at approx. 0.5 mb (50 $Nm^{-2}$), the fractions being collected as indicated below.

| Fract. No. | Head Temp (° C.) | Pot Temp (° C.) | Volume | Weight (g) |
|---|---|---|---|---|
| 1 | 43–68 | 103–108 | 10 ml | 8.9 |
| 2 | 68–70 | 108–109 | 10 ml | 9.1 |
| 3 | 70–74 | 109–110 | 10 ml | 9.1 |
| 4 | 74–74 | 110–110 | 10 ml | 9.2 |
| 5 | 74–74 | 110–114 | 10 ml | 9.4 |
| 6 | 74–74 | 114–114 | 10 ml | 9.2 |
| 7 | 74–75 | 114–115 | 12 ml | 11.8 |
| 8 | 75 | 115–115 | 10 ml | 9.3 |
| 9 | 75 | 115 | 10 ml | 9.7 |
| 10 | 75 | 115 | 10 ml | 10.2 |
| 11 | 75 | 115 | 50 ml | 46.1 |
| 12 | 75 | 118 | 50 ml | 46.5 |
| 13 | 75 | 120 | 55 ml | 52.0 |
| 14 | 75 | 125 | 50 ml | 46.2 |
| Resid. | | | | 26.0 |

All fractions were analysed by GC and assessed by odour quality, giving a bulking of ions 9–14 as pure product i.e. 210.7 g.

The bulking was analysed by GC and found to be: 3 peaks - - - (1). 65.6% Kovats 1417, (2) 25.9% Kovats 1422, (3). 3.0% Kovats 1431.

$^{13}C$ NMR of this bulking 17.175 ($CH_3$ of isopropyl), 17.205 ($CH_3$ of isopropyl), 17.289 ($CH_3$-2 posit. on ring), 23.131 ($CH_3$-4 posit on ring), 24.072 ($CH_3$-1 posit on ring), 26.396 ($CH_2$), 27.352 ($CH_2$) 28.147 (CH of isopropyl), 38.095 (CH in ring), 39.035 (C-quart), 79.056 (CH—OH), 127.007 (C=C), 130.746 (C=C).

GC analysis on HP Chiral-B (10% permethylatedbetacyclodextrin) gave the following isomer ratio: 6 peaks: 66.1%, 13.6%, 7.3%, 5.5%, 1.6%, 1.6%.

Other compounds in accordance with the invention can be made in analogous manner, using the approach of Example 1 or Example 2.

What is claimed is:

1. A compound having the structure

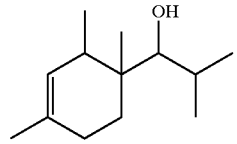

2. A perfume comprising the compound in accordance with claim 1, in an olfactively effective amount.

3. A perfume according to claim 2, wherein the compound is present in an amount of at least 0.01% by weight.

4. A perfume according to claim 3, wherein the compound is present in an amount in the range 0.1 to 80% by weight.

5. A perfumed product comprising the compound according to claim 1 or a perfume according to any one of claims 2, 3 or 4.

6. A method of making a compound in accordance with claim 1, comprising reduction of a ketone.

7. A method according to claim 6, wherein the compound of claim 1 is prepared by reduction of 2-methyl-1-(1,2,4-trimethyl-3-cyclohexen-1-yl)-1-propanone.

8. A method according to claim 6 or 7, wherein the ketone is prepared by Diels-Alder reaction of a diene and dienophile.

9. A method according to claim 8, wherein 2-methyl-1-(1,2,4-trimethyl-3-cyclohexen-1-yl)-1-propanone is prepared by Diels-Alder reaction of 2-methyl-1,3-pentadiene and 2,4-dimethyl-1-penten-3-one.

* * * * *